United States Patent
Kakimoto et al.

(10) Patent No.: US 6,514,908 B1
(45) Date of Patent: Feb. 4, 2003

(54) METHOD FOR EXCHANGE OF CATALYSTS

(75) Inventors: Yukihiko Kakimoto, Yokohama (JP); Yoshihisa Oka, Chigasaki (JP); Kenji Muraoka, Kawasaki (JP)

(73) Assignee: Nippon Shokubai Co Ltd, Osaka (JP)

( * ) Notice: Subject to any disclaimer, the term of this patent is extended or adjusted under 35 U.S.C. 154(b) by 21 days.

(21) Appl. No.: 09/632,090

(22) Filed: Aug. 2, 2000

(30) Foreign Application Priority Data

Aug. 4, 1999 (JP) .......................................... 11-221615

(51) Int. Cl.$^7$ .................................................. B01J 8/00
(52) U.S. Cl. ...................................... 502/439; 423/659
(58) Field of Search ........................... 423/659; 502/439

(56) References Cited

U.S. PATENT DOCUMENTS

| | | | | |
|---|---|---|---|---|
| 4,158,036 A | * | 6/1979 | Jaffe et al. .................. | 422/142 |
| 5,520,891 A | * | 5/1996 | Lee ............................. | 422/200 |
| 5,567,392 A | * | 10/1996 | Becker et al. ............... | 422/174 |
| 6,046,343 A | * | 4/2000 | Mummey et al. ........... | 549/259 |
| 6,300,507 B2 | * | 10/2001 | Oka et al. .................... | 549/536 |

* cited by examiner

Primary Examiner—Stanley S. Silverman
Assistant Examiner—Edward M. Johnson
(74) Attorney, Agent, or Firm—Sherman & Shalloway

(57) ABSTRACT

In the case where a carbon steel shell and tube type reactor is used and, for example, ethylene is subjected to catalytic gaseous oxidation to manufacture ethylene oxide, if rust is formed on the internal surface of the tubes, impurities such as aldehydes are formed. The cause of formation of the rust is that when the catalyst in the reactor is exchanged, dew is formed on the internal surface of the tubes. The present invention provides, as a method for preventing the rust formation, a method which comprises, in conducting the catalyst exchange work, maintaining the temperature of the internal surface of the tubes higher than the dew point at the work atmosphere (for example, filling the shell side with water and maintaining the temperature of the water higher than the temperature of the atmosphere).

2 Claims, No Drawings

METHOD FOR EXCHANGE OF CATALYSTS

TECHNICAL FIELD TO WHICH THE INVENTION BELONGS

This invention relates to a method for an exchange of catalysts. Detailedly, the invention relates to a method for an exchange of catalysts in a carbon steel shell and tube type reactor, which method is fit to manufacture an objective product of high quality and low in its impurity content. More detailedly, the invention relates to a method for an exchange of catalysts in a carbon steel shell and tube type reactor, which method is fit to prepare an objective product of high quality and low in impurities such as aldehydes through catalytic gaseous oxidation of a hydrocarbon compound.

PRIOR ART

Manufacturing technology of ethylene oxide has been already advanced in pretty high level, but increasing its selectivity even if the degree is as small as on the order of 1 to 2% is industrially desirable in view of the large production scale of ethylene oxide. It is also industrially desired to manufacture of ethylene oxide of high quality by lowering the content of impurities such as aldehydes which are difficult to separate and remove by distillation.

For manufacture of ethylene oxide by catalytic gaseous oxidation of ethylene a shell and tube type reactor is generally used. This shell and tube type reactor has hitherto been made of stainless steel, but, in recent years, inexpensive carbon steel reactors have come to be used.

However, when ethylene oxide is manufactured through gaseous oxidation of ethylene using a carbon steel reactor, the content of impurities such as aldehydes which is difficult to separate and remove by distillation or the like, sometimes, increases and ethylene oxide of high quality cannot be obtained.

The present inventors have made sequential researches into this problem, and as a result, they found that when rust is formed on the internal surface of the tubes (reaction tubes), impurities such as aldehydes are formed during the oxidation reaction, and the formation of this rust is due to water as dew formed on the internal surface of the tubes during the work of exchange of catalysts in the reactor, namely during the work of charging the catalyst or discharge the catalyst.

As methods for preventing rust formation due to dew formation during the catalyst exchange work, there can be considered a method which comprises shutting off contact between the internal surface of the tubes and the outside air by continuously sending dry air into the tubes during the work and preventing the outside air from coming in, but dew formation cannot sufficiently be prevented by this method. As another method, there is a method which comprises preventing formation of rust by periodically blowing dry air into the tubes to remove water as dew formed, but this method needs many times of blowing operation and dew formation cannot sufficiently be prevented thereby.

Problems to be Solved by the Invention

An object of the invention lies in improving disadvantages in the usual catalytic gaseous oxidation method using a carbon steel reactor by providing a method for exchange of catalysts fit for manufacturing an objective product of high quality and low in its impurity content. Another object of the invention lies in providing a method for effectively preventing dew formation onto the internal surface of the tubes in exchanging the catalyst in the carbon steel shell and tube type reactor.

Means for Solving the Problems

The present inventors found that, in exchanging the catalyst in the tubes, when, for example, the shell side is filled with water and the temperature of the water is maintained higher than the atmospheric temperature, the temperature of the internal surface of the tubes is maintained higher than the dew point of the atmosphere, and dew formation from moisture in the atmosphere and formation of rust can effectively be prevented.

Thus, according to the invention, a method for exchange of catalysts is provided which comprises, in conducting catalyst exchange work in a carbon steel shell and tube type reactor, maintaining the temperature of the internal surface of the tubes higher than the dew point of the outside air.

Embodiments of Practice of the Invention

Usually, catalyst exchange work is conducted in the atmosphere. The method of the invention is characterized in maintaining the temperature of the internal surface of the tubes higher than the dew point of the atmosphere at the time of work. More specifically, the method of the invention is characterized in maintaining the temperature of the internal surface of the tubes higher than the temperature of the outside air.

In the invention, for maintaining the temperature of the internal surface of the tubes higher than the temperature of the outside air, a heat transfer medium is charged at the shell side, and the temperature of this heat transfer medium is maintained at temperatures at least 2° C. higher than the temperature of the outside air, more specifically at temperatures 2 to 40° C. higher than the temperature of the outside air, preferably at temperatures 5 to 20° C. higher than the temperature of the outside air.

As the above-mentioned heat transfer medium, there can be used not only air or water but also kerosine, tetralin, diphenyl ether, Dowtherm® (trade name), etc.

In an embodiment of the invention, air of a temperature at least 2° C. higher than the temperature of the outside air is introduced into the shell side. In another embodiment of the invention, the shell side is filled with water, and the temperature of the water is maintained at least 2° C. higher than the temperature of the outside air. In view of easiness of handling, the latter embodiment using water is preferred.

The work of catalyst exchange itself can be carried out, with no particular limitation, according to a conventional method. For example, the catalyst is taken out from the inside of the tubes, and, if necessary after dry air is blown, a catalyst is charged inside the tubes. It is preferred to carry out the method of the invention at the time of the work of charge and/or discharge of the catalyst, particularly at the time of the work of charge and discharge.

As reaction using a carbon steel shell and tube type reactor, besides manufacture of ethylene oxide by oxidation of ethylene, there can be mentioned oxidation reaction and oxidative dehydro-genation reaction for manufacture of acrylic acid, maleic acid, phthalic anhydride, maleic anhydride, acrylonitrile, etc., and the like. The method of the invention can be applied to catalyst exchange in carbon steel shell and tube type reactors used in these reactions.

Dew formation onto the internal surface of the tubes at the catalyst exchange work is particularly frequent in the summer season and the rainy season when it is in high temperature and high humidity. Therefore, the method of the invention is particularly suitably used at catalyst exchange under high temperature and high humidity.

Effect of the Invention

According to the invention, dew formation at work of exchange of catalysts and subsequent formation of rust can efficiently be prevented by a convenient method. Thereby, the problems of formation of impurities due to the formation of rust, etc. are solved, and, for example in manufacture of ethylene oxide through oxidation of ethylene, ethylene oxide of high quality can be obtained.

In addition, according to the invention, it can effectively be prevented that inconveniences such as lowering of catalyst performance, particularly lowering of selectivity in oxidation reaction occurs by contact of water as the formed dew onto the catalyst.

Thus, by carrying out catalyst exchange according to the method of the invention, an objective oxidation product of high quality can be manufactured stably over a long period.

EXAMPLE

The present invention is further specifically described according to examples.

Example 1

A monotubular reaction tube with a shell of inside diameter 35 mm and length 14,000 mm was used as a pilot reactor. Exchange work of a silver catalyst for manufacture of ethylene oxide and gaseous oxidation reaction were carried out according to the following procedure.
(i) After the catalyst was discharged from the reaction tube, the reaction tube was left alone in a state of opening to the atmosphere over a period of 8 days.
(ii) Then, air blow into the reaction tube was made for one hour.
(iii) Then, a catalyst of the same kind was charged into the reaction tube, and the reaction tube was left alone in a state of opening to the atmosphere over a period of 8 days.
(iv) Then, an ethylene-containing gas was introduced into the reaction tube and gaseous oxidation reaction was carried out for 3 days.

In the case of the pilot reactor, discharge and recharge of the catalyst can be made in an extremely short time, but in the case of a large reactor for industrial production, it frequently takes work time of about 8 days, in a state of opening to the atmosphere, for discharge and recharge of the catalyst respectively. Therefore, in order to make the condition of the experiment carried out using the pilot reactor comparable with a real work condition in the case of using a large reactor for industrial production, a leaving-alone-term of 8 days in a state of opening to the atmosphere was set in each of the steps (i) and (iii).

During the term of the above procedure (iii), the shell side was filled with water and thereby the temperature of the internal surface of the tubes was maintained at 40° C. The temperature of the outside air at the time of work was maximally 33° C. and minimally 24° C.

The recharge of the catalyst was made as follows. Namely, an inert filler of diameter 10 mm was charged in the inlet preheating zone located 700 mm from the raw material gas inlet side, and a ring-shaped silver catalyst in such a state that its activity got stable by use in reaction for about one year was charged downstream thereof.

The condition of the gaseous oxidation reaction was as follows.

Space velocity (1/hr): 4,880
Inlet gas
 Temperature (° C.): 100
 Pressure ($kg/cm^2G$): 25.0
 Ethylene (vol %): 23.1
 Oxygen (vol %): 7.5
 $CO_2$ (vol %): 6.5
 Others (argon, nitrogen, methane, etc.) (vol %): 62.9
Outlet gas
 Temperature (° C.): 230
 Ethylene oxide (vol %): 2.0

After the reaction for 3 days, the aldehyde concentration in the outlet gas was 3 ppm. When after the completion of the reaction, the pilot tube was opened and the inside was examined, formation of rust was not observed on the internal surface of the tube.

Comparative Example 1

Except that the warming retention of the internal surface of the tube during the term of the above procedure (iii) was omitted, oxidation reaction was carried out in the same manner as in Example 1.

After the reaction for 3 days, the aldehyde concentration in the outlet gas was 10 ppm. When after the completion of the reaction, the reaction tube was opened and the inside was examined, formation of rust was observed on the internal surface of the tube.

It is understood from the results of Example 1 and Comparative example 1 that ethylene oxide of high quality can be manufactured according to the method of the invention.

What is claimed is:
1. A method for exchange of silver catalysts for manufacture of ethylene oxide by gaseous oxidation of ethylene which comprises, in conducting catalyst exchange work in a carbon steel shell and tube reactor, maintaining the temperature of the internal surface of the tube of the reactor higher than the dew point at work atmosphere, thereby inhibiting the formation of rust on the internal surface of the tube during catalyst exchange and inhibiting the formation of impurities during the oxidation reaction.
2. The method according to claim 1 wherein a heat transfer medium is put in the shell of the reactor and the temperature of the heat transfer medium is maintained at least 2° C. higher than the temperature of outside air.

* * * * *